United States Patent

Parkin

[11] Patent Number: 5,951,528
[45] Date of Patent: Sep. 14, 1999

[54] HYPODERMIC NEEDLES

[76] Inventor: Adrian Parkin, 34 Tredgold Avenue, Bramhope, Leeds, United Kingdom, LS16

[21] Appl. No.: 08/822,905

[22] Filed: Mar. 24, 1997

Related U.S. Application Data

[63] Continuation of application No. 08/142,365, Mar. 24, 1994, abandoned.

[30] Foreign Application Priority Data

May 22, 1991 [GB] United Kingdom ............ 9111049
May 21, 1992 [GB] United Kingdom .... PCT/GB92/00923

[51] Int. Cl.⁶ ............................................. A61M 5/00
[52] U.S. Cl. .................. 604/239; 604/272; 604/187; 600/4
[58] Field of Search ................ 604/164, 158, 604/239, 272–274, 181, 187; 128/654, 655; 600/431, 432, 5, 420, 3, 4

[56] References Cited

U.S. PATENT DOCUMENTS

| | | |
|---|---|---|
| 422,436 | 3/1890 | Otto . |
| 1,465,851 | 1/1923 | Kress . |
| 2,187,259 | 1/1940 | Barnhart ........................... 128/221 |
| 2,828,744 | 4/1958 | Hirsch et al. ...................... 128/221 |
| 2,844,149 | 7/1958 | Gettig . |
| 2,845,068 | 7/1958 | Gabriel . |
| 3,099,988 | 8/1963 | Ginsburg . |
| 3,155,090 | 11/1964 | Holter . |
| 3,358,684 | 12/1967 | Marshall . |
| 3,628,523 | 12/1971 | Pirtle, Jr. ................................ 128/2 |
| 3,921,864 | 11/1975 | Dawes . |
| 3,993,079 | 11/1976 | Henriques de Gatztanondo . |
| 4,202,332 | 5/1980 | Tersteegen et al. . |
| 4,335,718 | 6/1982 | Calabrese ........................... 128/218 N |
| 4,384,579 | 5/1983 | Lucas . |
| 4,405,314 | 9/1983 | Cope . |
| 4,629,450 | 12/1986 | Suzuki et al. . |
| 4,652,256 | 3/1987 | Vaillancourt . |
| 4,677,980 | 7/1987 | Reilly et al. ........................ 128/655 |
| 4,758,234 | 7/1988 | Orentreich et al. ................. 604/232 |
| 4,767,407 | 8/1988 | Foran . |
| 4,781,683 | 11/1988 | Wozniak et al. .................... 604/110 |
| 4,781,691 | 11/1988 | Gross .................................. 604/164 |
| 4,909,800 | 3/1990 | Gross . |
| 5,002,535 | 3/1991 | Gross . |
| 5,092,848 | 3/1992 | deCiutiis ............................. 604/170 |
| 5,234,438 | 8/1993 | Semrad ............................... 606/108 |
| 5,484,422 | 1/1996 | Sloane, Jr. et al. ................. 604/272 |
| 5,520,642 | 5/1996 | Bigagli et al. ...................... 604/88 |
| 5,527,291 | 6/1996 | Zadini et al. ....................... 604/165 |
| 5,743,872 | 4/1998 | Kelly .................................. 604/49 |
| 5,792,099 | 8/1998 | De Camp et al. .................. 604/51 |

FOREIGN PATENT DOCUMENTS

| | | |
|---|---|---|
| 24 08 852 | 9/1975 | Germany . |
| 641965 | 1/1979 | Russian Federation . |
| 542619 | 1/1942 | United Kingdom . |

*Primary Examiner*—Corrine McDermott
*Assistant Examiner*—Cris L. Rodriguez
*Attorney, Agent, or Firm*—Bacon & Thomas, PLLC

[57] ABSTRACT

A multi-diameter hypodermic needle, including a thin walled tubing with at least two sections having different internal diameters, is used to inject a X-ray contrast fluid in a rapid manner such that a subsequent image of the injected area evinces enhanced contrast characteristics.

28 Claims, 2 Drawing Sheets

HYPODERMIC NEEDLES

This application is a continuation of application Ser. No. 08/142,365, filed Mar. 24, 1994 now abandoned.

BACKGROUND OF THE INVENTION

This invention relates to hypodermic needles.

The invention is particularly applicable to hypodermic needles for use with syringes for delivering intravenous fluids such as X-ray contrast fluids, drugs, blood products, and other fluids in situations where high flow rates are required or where the viscosity of the fluid to be injected is high. In a general context, the hypodermic needle of the invention is applicable for administering fluids via veins, arteries, intramuscular injections, intrathecal injections, and in other situations where the use of high flow or a fine needle would be an advantage The hypodermic needle of the invention is thus applicable in medical, dental, pharmaceutical and in veterinary practises.

The hypodermic needle of the invention may also have applications in other areas, for example in the chemical, petrochemical and engineering industries.

The streamline flow of fluid in a tube is defined by Pouseuille's formula as:

$$\text{Flow} = \frac{(P_2 - P_1)\pi r^4}{8\mu l}$$

where:

$P_2 - P_1$ is the pressure difference between the ends of the tube r is the internal radius of the tube $\mu$ is the viscosity of the fluid l is the length of the tube In order therefore to increase the flow in the tube, the possibilities are:

(i) to increase the pressure difference;
(ii) to increase the radius of the tube;
(iii) to decrease the length of the tube;
(iv) to decrease the viscosity of the fluid.

The injection of viscous fluids in the medical field has posed problems for many years, since the length and the diameter of the needle are fixed by practical considerations. For example, in order to minimize discomfort to the patient and to be able to gain access to small veins, it is desirable to use needles with as small an external diameter as possible. There is a practical limit to the minimum length that a needle needs to be in order to gain access to deep veins. The viscosity of the fluid to be injected often cannot be changed. Thus the only parameter which can conveniently be varied, in order to increase the flow of the fluid, is the pressure.

To this end, mechanical injectors and levers have been used in order to increase the pressure, but the pressure still has to be limited by safety considerations when injecting into patients.

SUMMARY OF THE INVENTION

The present invention therefore seeks to provide an improved form of hypodermic needle which will obviate the disadvantages of known hypodermic needles by substantially reducing the force required to inject the fluid. The invention seeks to minimize the length of narrow tubing of the pointed end of the needle and to maximize the internal radius of this narrow tubing by using thin walled tubing. It will be noted from Pouseille's equation that an increase in the internal radius of the tube of only 10% will result in an increase in the flow by a factor of $$\left[\frac{110}{100}\right]^4,$$

i.e. an increase of almost 50 per cent. This is therefore a much more effective way to increase the flow than increasing the delivery pressure.

According to the present invention there is provided a multi-diameter hypodermic needle.

Preferably, the hypodermic needle will comprise tubing of two different diameters which are connected together in series. The tubing will preferably be of circular cross-section.

The hypodermic needle will preferably include a first section of thin walled small diameter tubing and a second section of thin walled tubing whose external diameter is less than the internal diameter of said first section, the first and second sections being fixedly secured together to prevent relative movement of said tube sections.

DETAILED DESCRIPTION OF THE PREFERRED EMBODIMENT

An outboard end of said first section will preferably be pointed.

The tubes of said first and second sections will preferably be composed of stainless steel.

In order that the invention may be more readily understood, embodiments thereof will now be described, by way of example, reference being made to the accompanying drawings, wherein.

Figure 1:
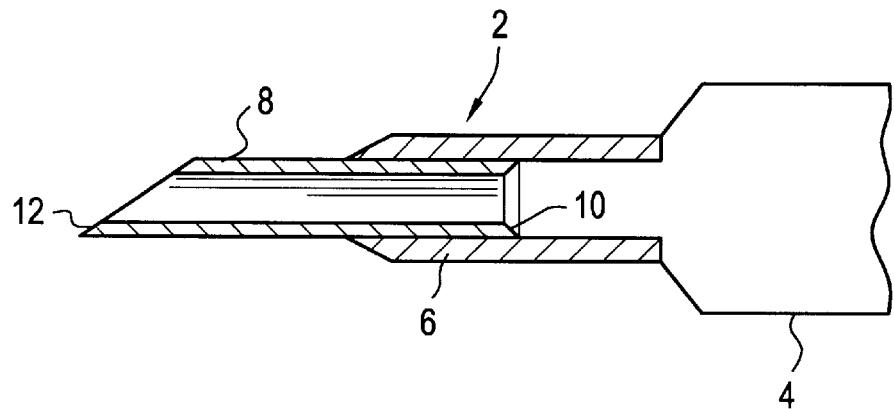
FIG. 1 is a longitudinal sectional elevation of a hypodermic needle in accordance with a first embodiment of invention.

Referring to the drawings, and firstly to FIG. 1, a hypodermic needle in accordance with the invention, indicated generally by reference numeral 2, comprised a luer 4 carrying a first section 6 of hollow tubing which in turn carries and from which projects a second section 8 of hollow tubing.

The section 6 is a length of thin walled stainless steel tubing, 18 gauge, and the section 8 is a length of thin walled tubing, 21 gauge, the sections being silver soldered together, as indicated by reference numeral 10, within the section 6 in order to prevent relative movement of said sections.

It will be appreciated that the sections 6 and 8 of tubing may be composed of materials other than stainless steel, for example alloys, plastics materials, glass, and other substances, and that other methods of securing the sections together may be utilized. In addition, gauges other than those specified may be used.

As will be seen the internal diameter of the section 8 is less than that of section 6. Specifically, the internal diameters for the 21 gauge and the 18 gauge stainless steel tubing used are nominally 0.025 inches and 0.036 inches respectively, and the outside diameters are nominally 0.032 inches and 0.049 inches. Thus the section 8 will locate comfortably within section 6.

The hypodermic needle thus has two internal diameters, the net result of which is that the force required to deliver fluid at a given rate from a syringe—not shown, but to which the needle is attached through the intermediary of the luer 4—is considerably reduced.

The outboard end of the section 8 is around to a point, as indicated by reference numeral 12, so that it can easily and readily pierce the skin.

Figure 2:
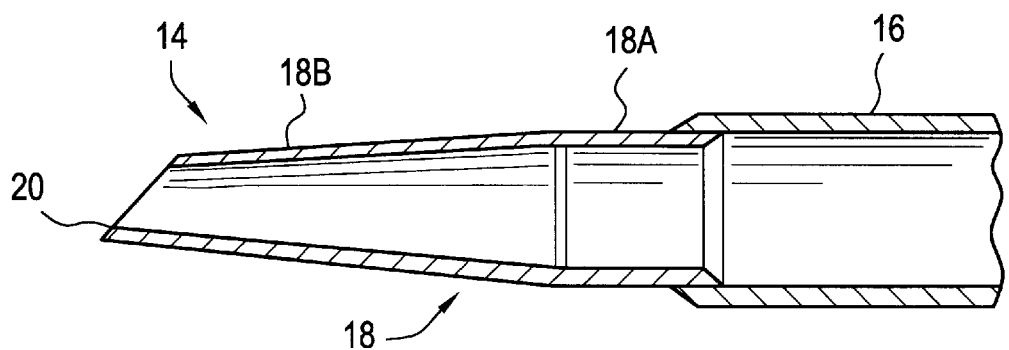
FIG. 2 is a longitudinal sectional elevation of a hypodermic needle in accordance with a second embodiment of the invention.

Referring now to FIG. 2, the hypodermic needle 14 comprises a first section 16 of constant internal diameter and a second section 18 having a first portion 18A of constant internal diameter and a second portion 18B whose internal diameter decreases from the first portion 18A to the pointed end 20 of the needle.

Figure 3:
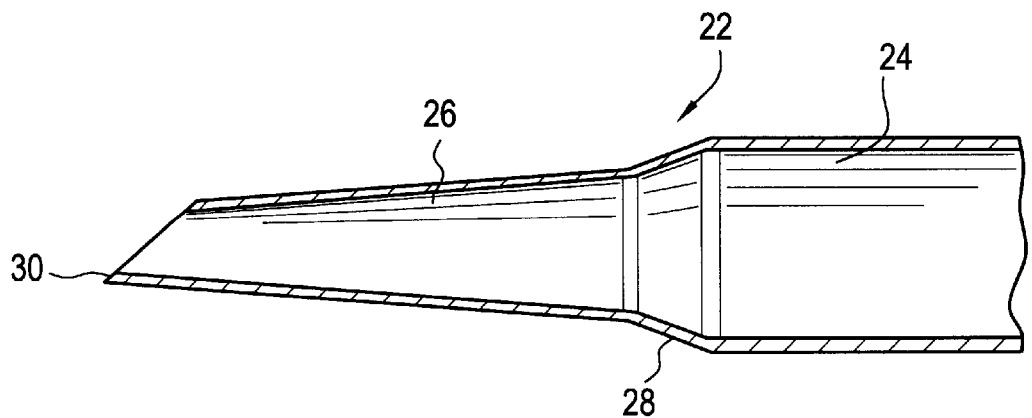
FIG. 3 is a longitudinal sectional elevation of a hypodermic needle in accordance with a third embodiment of the invention.

FIG. 3 shows a hypodermic needle 22 of unitary construction. The needle consists of a first section 24 and a second section 26 connected together by an integral shoulder 28. The internal diameter of the second section 26 decreases from the shoulder 28—whose internal diameter is tapered—to the pointed end 30 of the needle.

Figure 4:
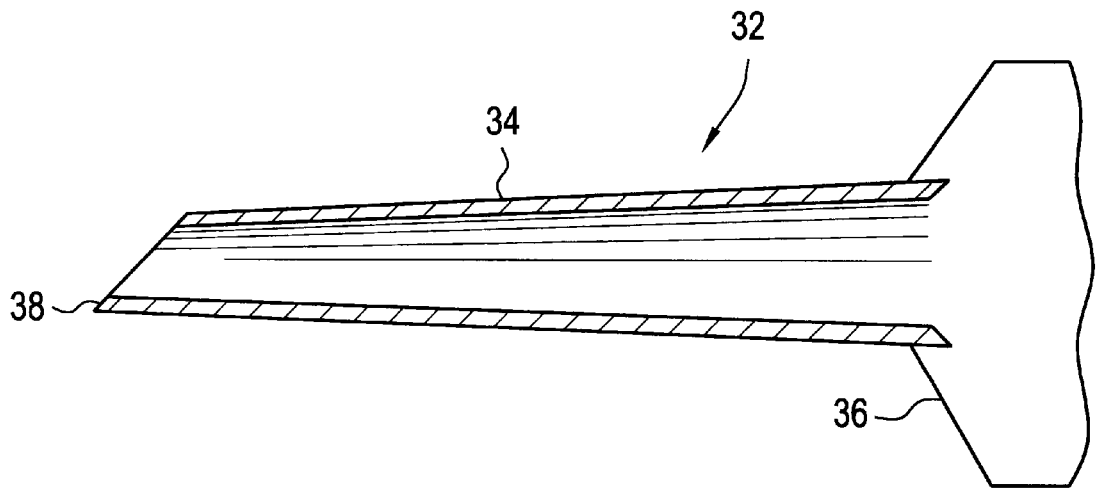
FIG. 4 is a longitudinal sectional elevation showing an alternative form of a hypodermic needle in accordance with the invention.

The hypodermic needle 32 of FIG. 4 consists of a single section 34 which is connected directly to a luer 36 which has a tapered internal diameter which decreases from the luer to the pointed end of the needle.

Figure 5:
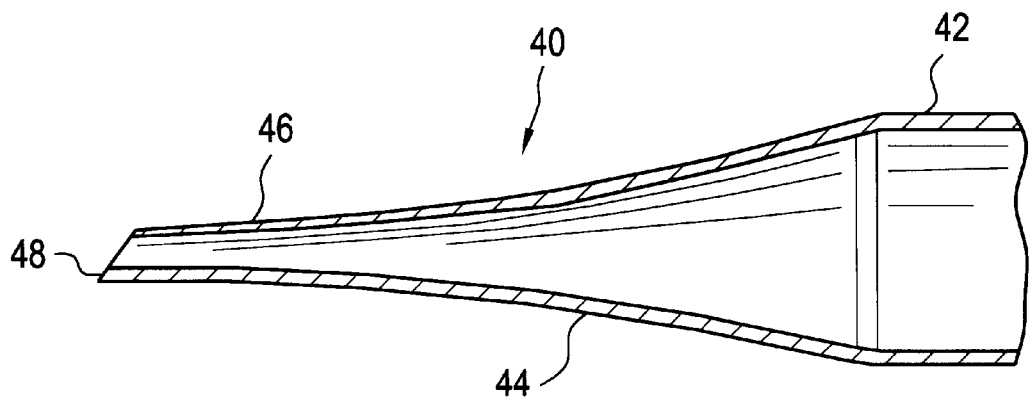
FIG. 5 is a longitudinal sectional elevation showing a further alternative form of a hypodermic needle in accordance with the invention.

The embodiment shown in FIG. 5 shows the hypodermic needle 40 of unitary construction and having a first section 42 and a second section 44 similar to that shown in FIG. 3, but having curved walls 46 and a curved tapering internal diameter, the taper again decreasing from the luer of the needle to the pointed end 48 of the needle.

The needles described above will preferably be composed of stainless steel, but alternatively they may be composed of alloys, plastics materials, glass, or other substances.

In a still further alternative embodiment of the present invention, the hypodermic needle may be formed from a single length of hollow tubing having two or more fixed internal diameters. The thickness of the wall of the tubing mast be constant or it may vary along the length of the needle.

Sample needles in accordance with FIG. 1 have been assembled and tested as follows:

Test Material
  60 ml syringe with luer lock connection, type Terumo
  hypodermic needle 21 G×1½, type Gilette
  new hypodermic needle, marked G 18B
  new hypodermic needle, unmarked
  weight 1.7 kg
  weight 2.5 kg
  stopwatch
  saline solution 0.9%, batch 060991
  Iodixanol injection 320 mg I/ml, batch number FF 011223.

Test Procedure
The syringe is filled with solution, saline or iodixanol injection. The hypodermic needle is connected to the syringe and the air is pressed out. The syringe is fixed in a holder and a weight, 1.7 kg or 2.5 kg, is put on the plunger. The solution flows through the hypodermic needle, and the time the plunger takes from the 40 ml mark to the 30 ml mark is measured. Flow is given as ml/min at 20° C.

Results
The results from the flow testing with saline is given in Table 1. The weight used when testing saline is 1.7 kg

TABLE 1

| HYPODERMIC NEEDLE | TIME (SECS) N = 5 | FLOW (ML/MIN) |
|---|---|---|
| 21 G × 1½ Gillette | 18.1 (17.7–18.4) | 33 |
| New hypodermic needle G 18 | 8.9 (8.7–9.0) | 67 |
| New hypodermic needle unmarked | 10.2 (9.9–10.5) | 59 |

The results from the flow testing with iodixanol injection 320 mg I/ml is given in Table 2. The weight used when testing iodixanol injection is 2.5 kg.

TABLE 2

| HYPODERMIC NEEDLE | TIME (SECS) N = 6 | FLOW (ML/MIN) |
|---|---|---|
| 21 G × 1½ Gillette | * | 0.13* |
| New hypodermic needle G 18 | 46.5 (44.0–49.9) | 13 |
| New hypodermic needle unmarked | 64.8 (61.0–70.0) | 9 |

*1 measurement gave as result 1 ml in 8 minutes

As expected, the needle in accordance with the invention showed in every case an increased flow for the same applied force and thus confers a distinct advantage over a standard hypodermic needle.

With a hypodermic needle in accordance with the invention, the force required to deliver a fluid at a given rate is considerably reduced. Alternatively, with a given force the flow rate is considerably increased. This is particularly useful where a high flow rate of the fluid is required or where the vicosity of the fluid is high, such as for example in the intravenous injection of an X-ray contrast fluid or in situations which are similar to such injections.

It will be understood that the needle may have more than two sections and more than two internal diameters.

Finally, whilst the invention has been described in relation to intravenous injections, it will be fully understood that a needle in accordance with the invention is equally applicable and useful in other situations.

I claim:

1. An apparatus for the injection of an X-ray contrast fluid comprising:
   a hollow body defining an internal cavity for housing fluid;
   a supply of X-ray contrast fluid contained in the cavity of said hollow body; and
   a multi-diameter hypodermic needle connected to and extending from said hollow body, said needle being in fluid communication with said internal cavity for delivering said supply of X-ray contrast fluid from said internal cavity.

2. An apparatus according to claim 1, wherein said needle comprises a first section of thin walled small diameter tubing attached to said hollow body and a second section of thin walled small diameter tubing, whose external diameter is less than the internal diameter of said first section, extending from said first section.

3. An apparatus according to claim 2, wherein the internal diameter of said first section is greater than the internal diameter of said second section.

4. An apparatus according to claim 3, wherein the internal diameter of said first section is constant and the internal diameter of said second section is constant but different from the internal diameter of said first section.

5. An apparatus according to claim 2, wherein said first and second sections are fixedly secured together to prevent relative movement between said first and second sections.

6. An apparatus according to claim 2, wherein said second section includes an end, remote from said hollow body, that is pointed.

7. An apparatus according to claim 2, wherein said first and second sections are each composed of stainless steel.

8. An apparatus according to claim 2, wherein said second section includes a first portion of constant internal diameter and a second portion having an internal diameter which decreases from said first portion.

9. An apparatus according to claim 2, wherein said tubing is of circular cross-section.

10. An apparatus according to claim 1, wherein said needle is of unitary construction and comprises a first portion of thin walled tubing of constant internal diameter extending from said hollow body and a second portion of thin walled tubing having an internal diameter which decreases from said first portion, said first and second portions being connected together by an integral shoulder.

11. An apparatus according to claim 1, wherein said needle comprises a single straight walled portion of thin walled tubing having an internal diameter which decreases towards an end of said needle remote from said hollow body.

12. An apparatus according to claim 1, wherein said needle comprises a single section of thin walled tubing having curved inner and outer walls and an internal diameter which decreases towards an end of said needle remote from said hollow body.

13. An apparatus according to claim 1, wherein said X-ray contrast fluid is viscous.

14. An apparatus according to claim 1, wherein said X-ray contrast fluid comprises an X-ray contrast agent having an iodine content of at least 320 mg I/ml.

15. An X-ray contrast fluid injection kit comprising: a container of X-ray contrast fluid and a multi-diameter hypodermic needle for use in injecting the X-ray contrast fluid housed in the container into a subject.

16. A kit according to claim 15, wherein said needle comprises a first section of thin walled small diameter tubing and a second section of thin walled small diameter tubing whose external diameter is less than the internal diameter of said first section.

17. A kit according to claim 16, wherein the internal diameter of said first section is greater than the internal diameter of said second section.

18. A kit according to claim 17, wherein the internal diameter of said first section is constant and the internal diameter of said second section is constant but different from the internal diameter of said first section.

19. A kit according to claim 16, wherein said first and second sections are fixedly secured together to prevent relative movement between said first and second sections.

20. A kit according to claim 16, wherein said second section has an end which is pointed.

21. A kit according to claim 16, wherein said first and second sections are each composed of stainless steel.

22. A kit according to claim 16, wherein said second section includes a first portion of constant internal diameter and a second portion having an internal diameter which decreases from said first portion.

23. A kit according to claim 16, wherein said tubing is of circular cross-section.

24. A kit according to claim 15, wherein said needle is of unitary construction and comprises a first portion of thin walled tubing of constant internal diameter and a second portion of thin walled tubing having an internal diameter which decreases from said first portion, said first and second portions being connected together by an integral shoulder.

25. A kit according to claim 15, wherein said needle comprises a single straight walled portion of thin walled tubing having an internal diameter which decreases towards an end of said needle.

26. A kit according to claim 15, wherein said needle comprises a single section of thin walled tubing having curved inner and outer walls and an internal diameter which decreases towards an end of said needle.

27. A kit according to claim 15, wherein said X-ray contrast fluid is viscous.

28. A kit according to claim 15, wherein said X-ray contrast fluid comprises an X-ray contrast agent having an iodine content of at least 320 mg I/ml.

* * * * *